United States Patent [19]
deCastro et al.

[11] Patent Number: 5,487,978
[45] Date of Patent: Jan. 30, 1996

[54] METHOD, COMPOSITION AND DEVICE FOR THE DETERMINATION OF CHOLESTEROL USING CHOLESTEROL OXIDASE OBTAINED FROM BACTERIAL STRAIN NRRL B-18713

[75] Inventors: Aurora F. DeCastro, Union, Mich.; Surendra K. Gupta, Elkhart, Ind.

[73] Assignee: GDS Technology, Inc., Elkhart, Ind.

[21] Appl. No.: 664,716

[22] Filed: Mar. 5, 1991

Related U.S. Application Data

[63] Continuation-in-part of Ser. No. 266,668, Nov. 3, 1988, abandoned.

[51] Int. Cl.⁶ .............................. C12Q 1/60; C12Q 1/28; C12N 9/04
[52] U.S. Cl. .................. 435/11; 435/19; 435/28; 435/190; 435/805
[58] Field of Search .................................. 435/11, 19, 28, 435/805, 810, 190

[56] References Cited

U.S. PATENT DOCUMENTS

| | | | |
|---|---|---|---|
| 3,907,642 | 9/1975 | Richmond | 435/11 |
| 4,503,144 | 3/1985 | Deeg et al. | 435/11 |

*Primary Examiner*—Ralph J. Gitomer
*Attorney, Agent, or Firm*—Browdy and Neimark

[57] ABSTRACT

The present invention provides a kinetic or rate method for the determination of cholesterol in free or bound form with of a cholesterol oxidase enzyme obtained from Bacterial strain NRRL B-18713 which inherently has a high Michaelis and Menton, Km, of about 10-2 to 10-3 M for cholesterol and optionally, of cholesterol esterase. The method can measure oxygen consumption, hydrogen peroxide or cholestenone formed. The present invention also provides a test composition for the kinetic determination of cholesterol, comprising cholesterol oxidase with an inherently high Km of about 10-2 to 10-3 M for cholesterol and optionally cholesterol esterase and a system for the determination of hydrogen peroxide, cholestenone or oxygen consumption.

23 Claims, No Drawings

METHOD, COMPOSITION AND DEVICE FOR THE DETERMINATION OF CHOLESTEROL USING CHOLESTEROL OXIDASE OBTAINED FROM BACTERIAL STRAIN NRRL B-18713

CROSS REFERENCE TO RELATED APPLICATIONS

This application is a continuation-in-part of U.S. application Ser. No 266,668 filed on Nov. 3, 1988 now abandoned.

FIELD OF THE INVENTION

This invention relates to a method, composition and device for the determination of cholesterol using a cholesterol oxidase which inherently has a high Km of about $10^{-2}$ to $10^{-3}$M for cholesterol and cholesterol esters, thus making it possible to carry out the determination kinetically.

BACKGROUND OF THE INVENTION AND DESCRIPTION OF THE PRIOR ART

It is now well established that an elevated cholesterol level in blood is an indicator of a higher risk of coronary heart disease (CHD). Therefore, there is an increased demand for measuring blood cholesterol levels for screening general populations and for monitoring patients who are on cholesterol reducing diets or drugs. Since the recent data from the College of American Pathologists (CAP) survey of 5,000 participating laboratories revealed that a great deal of inaccuracy exists in reporting of cholesterol test results, it has become evident that there is an urgent need for an improved cholesterol test which will yield accurate and reliable results (Naito, H.K. and Hartmann, A.E., "The ABC's of Cholesterol Standardization", by the College of American Pathologists, 1987).

Conventionally, cholesterol is measured by direct or indirect chemical methods (U.S. Pat. Nos. 3,001,950; 3,479,154; 3,558,516) which involve the handling of highly corrosive material. Therefore, direct enzymatic methods today have virtually replaced the chemical methods in clinical laboratories. These enzymatic methods involve a) hydrolysis of cholesterol esters by an esterase or a combination of lipase and esterase (U.S. Pat. Nos. 3,776,816; 3,884,764; 3,925,164), b) subsequent oxidation of cholesterol by cholesterol oxidase (U.S. Pat. No. 3,907,645) which uses oxygen and produces cholestenone and hydrogen peroxide and c) quantitative measuring of hydrogen peroxide thus produced by means of peroxidase and reduced chromogen as shown below:

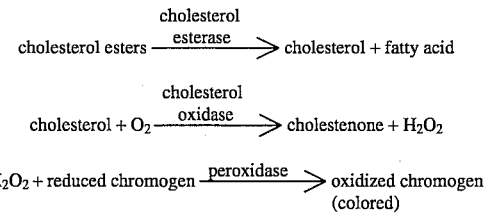

Alternatively, instead of measuring the hydrogen peroxide produced, the cholestenone produced or the oxygen consumed can be measured in this reaction to determine the level of cholesterol present in the sample. This enzymatic approach has admittedly brought considerable advancement in the determination of cholesterol due to its specificity, sensitivity and convenience when compared with previously used chemical methods. The process, however, has not been suitable for a rapid, kinetic (rate) method.

Cholesterol oxidases catalyze the most specific part of the reaction sequence in the determination of cholesterol. These cholesterol oxidases are obtained from organisms such as Nocardia, Brevibacterium or Streptomyces (U.S. Pat. Nos. 3,907,642; 3,983,005; 4,212,938; 4,226,713; 4,229,527; 4,350,762) and have a low Km (Michaelis and Menton) value of $10^{-4}$ to $10^{-5}$M for cholesterol. The low Km values of these cholesterol oxidases do not allow the reaction to proceed as first order or pseudo-first order at a concentration range of up to 13 mmoles/L cholesterol, which is the range of interest for serum concentration. Therefore, the enzymatic methods developed with these cholesterol oxidases are "end-point" methods where all of the cholesterol is titrated by an excess of cholesterol oxidase. The "end-point" methods generally take 6 to 10 minutes to perform, require sample blanks and are subject to interferences by turbidity, bilirubin, hemolysis, ascorbate, and so forth. Some of these problems can be avoided and the cholesterol measurement further improved by developing "kinetic" or "rate" methods as an alternative to "end-point" methods. However, to develop a rapid and convenient kinetic" method for the cholesterol determination, a first order or pseudo-first order reaction is required. This can only be achieved if one has available a cholesterol oxidase with a Km of $10^{-2}$ to $10^{-3}$M for cholesterol, i.e., a Km of about 20–100 fold larger than the substrate concentration of interest, thus making the reaction rate limiting. In this case the reaction will follow pseudo-first order kinetics.

The kinetic method thus developed can offer many advantages over end point methods, such as, 1) reduction in analysis time; 1–2 minutes, 2) less interference by turbidity, bilirubin, hemolysis and ascorbate, 3) obviate the need for a sample blank, and 4) offers improved accuracy.

Such a kinetic method for cholesterol determination was successfully developed by Deeg, et al. (U.S. Pat. No. 4,503,144) where the inventors were able to artificially increase the Km of cholesterol oxidase from genus Streptomyces which has a Km of $10^{-4}$ to $10^{-5}$ moles/L by adding a competitive inhibitor, such as, 3,4-dichlorophenol. By manipulating the concentration of 3,4-dichlorophenol and cholesterol oxidase, it was possible to increase the Km of the enzyme allowing the cholesterol oxidase reaction to proceed as pseudo-first order.

In contrast to Deeg et al., the present invention utilizes a new and unique cholesterol oxidase (GDS-41) isolated from a mutant of genus Nocardia which was found surprisingly to have an inherent Km value of $10^{-2}$ to $10^{-3}$M for cholesterol. Therefore, it is the object of the present invention to provide a kinetic method and a test composition for the determination of cholesterol using this cholesterol oxidase. This invention provides a significant advantage over the previously described Deeg, et al. method as it does not require artificially increasing the Km value by using a competitive inhibitor and therefore, requires only about one tenth to one hundredth the amount of cholesterol oxidase normally used in a prior art test composition. As cholesterol oxidase is usually the most expensive ingredient in the test composition, this method will allow the development of a more cost effective cholesterol test. In addition, the method allows measuring the reaction rate within 0.5–1.5 minutes, thus permitting higher throughput using automatic clinical analyzers or alternatively, providing immediate results for use in "on-site" or physicians office testing.

SUMMARY OF THE PRESENT INVENTION

The present invention basically involves a test composition, method and device for the kinetic determination of cholesterol utilizing a new and unique cholesterol oxidase having an inherent Michaelis and Menton constant, Km, of from about $10^{-2}$ to $10^{-3}$ and a means for detecting a reaction product of the action of this enzyme on cholesterol in the presence of oxygen, such as, for example, detecting the peroxide formed using a reagent such as peroxidase and a chromogen, determining the cholestenone formed or the oxygen consumed.

PREFERRED EMBODIMENTS OF THE PRESENT INVENTION

According to the present invention, a composition, method and test device is provided for the determination of cholesterol in free or bound form by means of cholesterol oxidase and optionally, cholesterol esterase by measurement of formed hydrogen peroxide or cholestenone or oxygen consumption, wherein the determination is carried out kinetically with the use of a cholesterol oxidase which has an inherent Km value of $10^{-2}$ to $10^{-3}$M.

The cholesterol oxidase (GDS-41) used in the present invention is developed from a mutant of Nocardia sp. which was deposited under Budapest treaty provisions on Sept. 21, 1990 at the Northern Regional Research Laboratory, U.S. Department of Agriculture, Peoria, Ill. and has been assigned deposit number NRRL B-18713.

As none of the previously known cholesterol oxidases from Nocardia, Brevibacterium or Streptomyces could be used as such, this new enzymatic method makes possible, for the first time, a kinetic determination of cholesterol without the presence of a competitive inhibitor.

The above noted first order reaction can be achieved with the use of fairly widely varying concentrations of cholesterol oxidase GDS-41; however, it is preferable to use 10 to 200 U/liter. The methodology of the present invention is carried out in the usual manner for kinetic determinations, i.e., two measurements are made in a previously determined time interval. The determination can be carried out in the pH value range where the enzyme is active, preferably in a buffered solution at a pH value from 6.0 to 8.5.

The scope of the present invention covers in principle the methods of measurement of all known variants of the cholesterol determination. The cholestenone formation can be measured by measuring the increase in absorbance at 230 to 250 nm wavelength. The rate of oxygen consumption can be measured by known means, such as using oxygen electrodes.

One preferred embodiment of the methodology of the present invention consists in the determination of hydrogen peroxide formed by the addition of peroxidase, 4-aminoantipyrine, phenol or phenol derivatives and a buffer substance suitable for the system. Appropriate buffers include phosphate buffer, tris buffer, hepes buffer [4-(2-hydroxyethyl)-1-piperazinoethane-sulphonic acid] and bicine buffer. In the case of this embodiment, inclusion of a non-ionic detergent and optionally, a detergent of the cholic acid group yields best results.

The present invention also provides a test composition or a reagent for the kinetic determination of cholesterol, comprising essentially the above mentioned cholesterol oxidase with a Km of $10^{-2}$ to $10^{-3}$ M. After the fluid being tested is contacted with this composition, a system for the determination of the cholestenone or hydrogen peroxide formed or the oxygen consumed is utilized. Optionally, cholesterol esterase is used in the test system.

A preferred means for the determination of hydrogen peroxide comprises a combination of 4-aminoantipyrine or a derivative thereof, such as phenol or phenol derivative, buffer and detergents. These systems, or modifications thereof, are advantageous as they measure a colored material at visible wavelengths. The test system preferably also contains a non-ionic detergent alone or optionally together with a detergent of the cholic acid group. The test system may also contain an appropriate buffer for optimizing enzymatic activity, preferably in the pH range of 6.0 to 8.5, such as phosphate buffer, tris buffer or hepes buffer.

A test composition or reagent according to the present invention which has proved to be especially preferred is one which has the following composition for the measurement of hydrogen peroxide.

| | |
|---|---|
| 10 to 1,000 U/L | cholesterol oxidase (Km of $10^{-2}$ to $10^{-3}$M) |
| 100 to 20,000 U/L | cholesterol esterase |
| 100 to 5,000 U/L | peroxidase |
| 0.5 to 10 mmoles/L | 4-aminoantipyrine or its derivative |
| 5.0 to 20 mmoles/L | phenol or phenol derivative |
| 0 to 10 g/L | non-ionic detergent |
| 0 to 30 mmoles/L | detergent of the cholic acid group and |
| 20 to 200 mmoles/L | buffer, pH 6.0 to 8.5 |

Specific illustrations are shown in Examples 1–4.

The test compositions of the present invention can also contain additional materials usual for enzymatic reagents such as stabilizing agents, for example mannitol, albumin, salts and bactericides such as azides.

In the above mentioned hydrogen peroxide measurement system, instead of phenol there can be used phenol derivatives, naphthol or naphthol derivatives, aniline or aniline derivatives, naphthylamine or naphthylamine derivatives, hydroxyquinolines, aminoquinolines, dihydroxy phenylacetic acid and similar reacting substances. The 4-aminoantipyrine can be replaced by methylbenzothiazolone-hydrazone, phenylenediamine sulfonate, sulfonated methylbenzothiazolone hydrazone derivatives and similarly reacting compounds.

Hydrogen peroxide can also be measured by other known systems including luminescent methods in which fluorescence or chemi-luminescence is measured; a system comprising catalase, a $\beta$-diketone such as acetylacetone, and an alcohol such as methanol or ethanol; or peroxidase and a chromophore such as tetramethyl benzidine or 2,3-aminobenzothiazoline-sulfonate; or an electrochemical method.

The test reagent in the present invention can also measure the formation of cholestenone by measuring the change in absorbance between 230 to 250 nm wavelengths, preferred at 240 nm wavelength or measuring oxygen consumption by oxygen electrodes or similar methods. The preferred composition has the following quantitative composition.

| | |
|---|---|
| 10 to 1,000 U/L | cholesterol oxidase (Km of $10^{-2}$ to $10^{-3}$M) |
| 100 to 20,000 U/L | cholesterol esterase |
| 0 to 10 g/L | non-ionic detergent |
| 0 to 30 mmoles/L | detergent of the cholic acid group and |
| 20 to 200 mmoles/L | buffer, pH 6.0 to 8.5 |

Specific illustrations are given in Examples 5 and 6.

The test reagent, according to the present invention, can be in a liquid form or it can be incorporated with a solid carrier or matrix such as bibulous paper. Such incorporation can comprise either simply impregnating the matrix with the reagent in a liquid system and drying the carrier such that it contains the dried residue of the reagent or the reagent can be chemically or physically immobilized in the matrix. In such cases, the measurement of cholesterol can be carried out a) by placing a sample on the reagent carrier, b) by dipping the carrier incorporated with the reagent into the sample or c) by eluting the reagent from the carrier with a definite volume of sample. The test system can measure the rate of reaction at a predetermined interval of time directly on the carrier, for example, by reflectance photometry or by measuring the luminescence generated by the reaction between the reagent and the cholesterol present in the test sample.

If the determination takes place after elution of the reagent the measurement can be conducted as in the case of the use of a carrier-free reagent.

The carrier or matrix materials are the conventional carriers such as paper, cellulose, porous synthetic resin membrane, fiber fleece and similar substances. The reagent can be applied either by spraying or layering the reagent on to the carrier, or by dipping the carrier into the reagent according to the present invention. A specific illustration is given in Example 7.

The method, according to the present invention, allows quicker measurement of cholesterol in a sample and thus provides the saving of time in comparison with conventional end point methods. It also provides increased output for auto analyzers and does not require a sample blank. Being a kinetic method it further reduces the interference from known interfering material such as turbidity, bilirubin, hemoglobin or ascorbate and is cost effective.

The following Examples are given for the purpose of illustrating the present invention.

EXAMPLE 1

The following test composition was employed:

| | |
|---|---|
| 50 U/L | cholesterol oxidase GDS-41 (Km of $10^{-2}$ to $10^{-3}$M) |
| 1500 U/L | cholesterol esterase |
| 500 U/L | peroxidase |
| 0.87 mmole/L | 4-aminoantipyrine |
| 2.2 mmoles/L | phenol |
| 10 mmoles/L | sodium cholate |
| 0.25% | non-ionic detergent (Triton x-100) |
| 100 mmoles/L | phosphate buffer, pH 7.6 |

The cholesterol determination in serum was measured at 37° C. by using a Gilford spectrophotometer at 505 nm; time delay: 30 seconds; interval: 1 minute; rate method, reagent used: 2 ml; sample used: 20 µl.

The determination gave a linear course of the curve up to at least 500 mg/dl (13 mmoles/L) level of cholesterol, as shown below.

| mg/dl Serum Cholesterol | Change in O.D.$_{min}$ (0.5–1.5 min) |
|---|---|
| 500 | 0.059 |
| 375 | 0.046 |
| 250 | 0.030 |
| 125 | 0.015 |

EXAMPLE 2

The following test composition was used:

| | |
|---|---|
| 100 U/L | cholesterol oxidase GDS-41 (Km of $10^{-2}$ to $10^{-3}$M) |
| 1500 U/L | cholesterol esterase |
| 500 U/L | peroxidase |
| 0.87 mmoles/L | 4-aminoantipyrine |
| 2.2 mmoles/L | phenol |
| 10 mmoles/L | chloate |
| 0.10% | non-ionic detergent (Triton X-100) |
| 50 mmoles/L | phosphate buffer, pH 7.0 |

The reagent was used as described in Example 1. In this example, cholesterol oxidase was increased from 50 U/L to 100 U/L and phosphate buffer was used at a pH 7.0 instead of pH 7.6. The following results were obtained.

| mg/dl Serum Cholesterol | Change in $OD_{505}$/(0.5–1.5 min) |
|---|---|
| 500 | 0.124 |
| 375 | 0.094 |
| 250 | 0.067 |
| 125 | 0.034 |

As in Example 1, a linear course was ascertained at least up to 500 mg/dl (13 mmoles/L) cholesterol.

EXAMPLE 3

The following test composition was used:

| | |
|---|---|
| 200 U/L | cholesterol oxidase GDS-41 (Km of $10^{-2}$ to $10^{-3}$M) |
| 1500 U/L | cholesterol esterase |
| 500 U/L | peroxidase |
| 0.87 mmoles/L | 4-aminoantipyrine |
| 2.2 mmoles/L | phenol |
| 10 mmoles/L | sodium cholate |
| 0.25% | non-ionic detergent (Triton X-100) |
| 100 mmoles/L | hepes buffer, pH 7.0 |

The reagent was used as described in Example 1. In this example, cholesterol oxidase was increased to 200 u/L and hepes buffer was used instead of phosphate buffer.

| mg/dl Serum Cholesterol | Change in $OD_{505}$/(0.5–1.5 min) |
|---|---|
| 500 | 0.235 |
| 375 | 0.180 |
| 250 | 0.120 |
| 125 | 0.061 |

As in previous Examples, a linear relationship was observed at least up to 500 mg/dl serum cholesterol.

EXAMPLE 4

The following reagent composition was used:

| | |
|---|---|
| 50 U/L | cholesterol oxidase GDS-41 (Km of $10^{-2}$ to $10^{-3}$M) |
| 1500 U/L | cholesterol esterase |
| 500 U/L | peroxidase |
| 2 mmoles/L | 4-aminoantipyrine |
| 10 mmoles/L | 3,4 dichloro-2-hydroxybenzenesulfonate |
| 10 mmoles/L | sodium cholate |
| 0.25% | non-ionic detergent (Triton x-100) |
| 100 mmoles/L | phosphate buffer, pH 7.6 |

This reagent was used as described in Example 1. In this example, a phenol derivative which has a molecular extinction of about 24,000 was used instead of phenol with a molecular extinction of 6,200.

| mg/dl Serum Cholesterol | Change in $OD_{505}$/(0.5–1.5 min) |
|---|---|
| 500 | 0.240 |
| 375 | 0.181 |
| 250 | 0.121 |
| 125 | 0.060 |

Again, a linear relationship was observed at least up to 500 mg/dl. The method showed a good precision with a cv of less than 1% (n=10).

EXAMPLE 5

Kinetic Determination with Measurement of the Cholestenone at 240 nm.

The following reagent was used:

| 100 U/L | cholesterol oxidase GDS-41 (Km of $10^{-2}$ to $10^{-3}$M) |
|---|---|
| 1500 U/L | cholesterol esterase |
| 0.10% | non-ionic detergent (Triton x-100) |
| 10 mmoles/L | sodium cholate |
| 100 mmoles/L | phosphate buffer, pH 7.6 |

In this example, serum cholesterol was measured by using a Gilford spectrophotometer at 37° C. The cholestenone formation was measured at 240 nm wavelength, initial time: $t_i$=0.5 min, final time: $t_f$=1 min; reagent volume: 2 ml; sample volume: 20 µl.

| mg/dl Serum Cholesterol | Change in $OD_{240}$/(0.5–1.5 min) |
|---|---|
| 500 | 0.120 |
| 375 | 0.091 |
| 250 | 0.063 |
| 125 | 0.030 |

The determination gave a linear relationship up to at least 500 mg/dl level of cholesterol.

EXAMPLE 6

Measurement of Oxygen Consumption

The following reagent was used:

| 100 U/L | cholesterol oxidase GDS-41 (Km of $10^{-2}$ to $10^{-3}$M) |
|---|---|
| 10 mmoles/L | sodium cholate |
| 100 mmoles/L | phosphate buffer, pH 7.6 |

When to a 2 ml of reagent 15 ul of sample was added and the rate of oxygen consumption measured electrochemically between the 1st and 2nd minute, the results were:

| Cholesterol Concentrations | Relative Reaction Rate |
|---|---|
| 125 mg/L | 25 |
| 250 mg/L | 50 |
| 375 mg/L | 75 |
| 500 mg/L | 100 |

EXAMPLE 7

A dry chemistry test was made by impregnating the following test reagents on 10×10 mm square filter paper.

| 75,000 U/L | cholesterol esterase |
|---|---|
| 5,000 U/L | cholesterol oxidase GDS-41 (Km $10^{-2}$ to $10^{-3}$M) |
| 50,000 U/L | peroxidase |
| 0.25 moles/L | sodium cholate |
| 50 ml/L | Triton x-100 |
| 100 mmoles/L | potassium phosphate, pH 7.0 |
| 3.5 g/L | 4-aminoantipyrine |
| 15 g/L | 3,5-dichloro-2-hydroxy benzenesulfonate |

When 10 µl of serum was added to the filter paper deeper shades of pink appeared corresponding to the increasing cholesterol concentration. The decrease in reflectance was proportional to the cholesterol concentration in the samples.

EXAMPLE 8

Preparation of Cholesterol Oxidase (GDS-41)

A loopful of the organism was transferred into a 250 ml flask containing 50 ml of sterile media consisting of 0.1% yeast extract, 0.2% potassium phosphate, 0.2% ammonium sulfate at a pH of 7.0. The flask was stirred at 200 rpm at 37° C. for 48 hours and the culture transferred to several 2.8 L flasks containing 1 to 1.5 L of the above sterile media containing 1 g/L cholesterol. The flasks were stirred at 200 rpm at 30° C. for 36 hours. The media were pooled and centrifuged at 8000 rpm for 30 minutes. Subsequently, cholesterol oxidase was checked in the supernatant using the following assay procedure: An assay mixture containing 1 ml of 0.3M potassium phosphate buffer, pH 7.0, 1 ml of peroxidase (18 units/ml), 0.5 ml of 4-aminoantipyrine (0.1%), phenol 0.5 ml (0.08M), 0.1 ml sodium cholate (0.3M) was prepared. To 3.0 ml of this assay mixture at 37° C., 0.5 ml of cholesterol solution (4.5 mg/ml in isopropanol) was added and the change on O.D. per minute measured at 500 µm wavelength. Enzyme activity in the supernatant was calculated to be 0.2–0.3 units/ml. The resultant enzyme was purified using known methods of DEAE ion-exchange chromatography and lyophilized. It had a Km of $5 \times 10^{-3}$M.

It is understood that the above specific examples are illustrative and not intended to limit the scope of the present invention.

What is claimed is:

1. A test composition for the kinetic determination of cholesterol comprising an effective amount of cholesterol oxidase for determining cholesterol in sample obtained from Bacterial strain NRRL B-18713 in a suitable carrier.

2. The composition according to claim 1 further including an effective amount of cholesterol esterase.

3. The composition according to claim 1 further including a buffer to maintain the pH of the composition in a range of from about 6 to about 8.5.

4. A composition according to claim 3 wherein the reagent includes 4-aminoantipyrine, phenol, and peroxidase.

5. The composition according to claim 4 further including a buffer capable of maintaining the composition in a pH range of from about 6 to about 8.5.

6. The composition according to claim 1 further including a detergent selected from the group consisting of nonionic and cholate detergents.

7. The composition according to claim 6 wherein said buffer is selected from the group consisting of phosphate, hepes, bicine, and tris buffers.

8. The composition according to claim 1 in the substantial absence of a competitive inhibitor.

9. In a method for the kinetic determination of cholesterol in a sample, the improvement comprising contacting said sample with cholesterol oxidase from Bacterial strain NRRL B-18713 to oxidize cholesterol to cholestenone.

10. The method according to claim 9 wherein the sample is further contacted with cholesterol esterase.

11. The method according to claim 10 wherein the reaction is conducted in a buffered solution at a pH in the range of from about 6 to about 8.5.

12. The method according to claim 11 wherein a detergent selected from the group consisting of nonionic and cholate detergents is added to the reaction.

13. The method according to claim 10 wherein at least two measurements of the reaction parameter are conducted at a predetermined time interval.

14. The method according to claim 9 further comprising measuring a reaction parameter selected from the group consisting of hydrogen peroxide formed, cholestenone formed, and oxygen consumed to achieve a pseudo-first order reaction.

15. The method according to claim 14 wherein oxygen consumption is measured by oxygen electrodes.

16. The method according to claim 14 wherein cholestenone formed is measured by measuring increase in absorbance at 230 to 250 nm.

17. The method according to claim 14 wherein hydrogen peroxide is measured spectrophotometrically at visible wavelengths.

18. The method according to claim 17 wherein the hydrogen peroxide is measured by contacting the sample with a reagent consisting essentially of an effective amount of phenol, 4-aminoantipyrine, peroxidase and a buffer selected from the group consisting of phosphate, hepes, tris and bicine buffers to enable measurement of color change.

19. The method according to claim 9 wherein the determination is conducted in the substantial absence of a competitive inhibitor.

20. In a test device for the kinetic determination of cholesterol comprising a solid carrier impregnated with a cholesterol oxidase and a reagent for measuring the response to a reaction between cholesterol oxidase and cholesterol in the presence of oxygen, the improvement comprising using cholesterol oxidase obtained from Bacterial strain NRRL B-18713.

21. The test device according to claim 20 wherein the solid carrier is further impregnated with cholesterol esterase.

22. The device according to claim 20 wherein said reagent comprises peroxidase, phenol, 4-aminoantipyrine and buffer for maintaining the pH of the system in a range of from about 6 to about 8.5.

23. The test device according to claim 20 wherein said carrier is paper.

* * * * *